US011395582B2

(12) United States Patent
Troller et al.

(10) Patent No.: US 11,395,582 B2
(45) Date of Patent: Jul. 26, 2022

(54) ENDOSCOPE WITH OPTIMIZED ILLUMINATION PATHWAY

(71) Applicant: Clear Image Technology, LLC, Westlake, OH (US)

(72) Inventors: Stefan Troller, Sissach (CH); Matthias Pfister, Bern (CH); Michel Saint-Ghislain, Düdingen (CH)

(73) Assignee: Clear Image Technology, LLC, Westlake, OH (US)

( * ) Notice: Subject to any disclaimer, the term of this patent is extended or adjusted under 35 U.S.C. 154(b) by 0 days.

(21) Appl. No.: 16/041,445

(22) Filed: Jul. 20, 2018

(65) Prior Publication Data

US 2019/0183325 A1 Jun. 20, 2019

Related U.S. Application Data

(60) Provisional application No. 62/599,197, filed on Dec. 15, 2017.

(51) Int. Cl.
*A61B 1/06* (2006.01)
*H04N 5/225* (2006.01)
(Continued)

(52) U.S. Cl.
CPC .......... *A61B 1/0684* (2013.01); *A61B 1/0011* (2013.01); *A61B 1/05* (2013.01); *A61B 1/051* (2013.01); *A61B 1/0607* (2013.01); *A61B 1/07* (2013.01); *G02B 6/0006* (2013.01); *H04N 5/2253* (2013.01); *H04N 2005/2255* (2013.01)

(58) Field of Classification Search
CPC .............. G02B 6/0006; H04N 5/2253; H04N 2005/2255; A61B 1/0684; A61B 1/0011; A61B 1/05; A61B 1/051; A61B 1/0607; A61B 1/07
See application file for complete search history.

(56) References Cited

U.S. PATENT DOCUMENTS

| 2003/0042493 A1* | 3/2003 | Kazakevich | ............ | F21V 13/14 257/98 |
| 2009/0086314 A1* | 4/2009 | Namba | .................. | G02B 21/34 359/383 |

(Continued)

*Primary Examiner* — Hesham K Abouzahra
(74) *Attorney, Agent, or Firm* — Law Office of Scott C Harris, Inc

(57) ABSTRACT

A medical imaging system, is formed of a lighting module, preferably using a single LED. The LED illuminates a reflection chamber, located to receive light from the LED, said reflection chamber terminating in a fiber interfacing surface. An optical fiber, connects to the fiber interfacing surface, and receives light therefrom when said LED is energized. The optical fiber has a first surface connected to the fiber interfacing surface, and has a second surface at an opposite end of the optical fiber from the first surface. A light guide, has a first end, optically coupled to the second end of said optical fiber, and the light guide directs light from the first end into a cone shaped surface at a second end, that directs light away from a center of the cone shaped surface into a hollow cylindrical shape of light, creating an illumination by the light at a distal end of the hollow cylindrical shape opposite the first end. A camera, mounted inside the light guide, within an inside of the cone shaped surface images the area illuminated by the light guide.

16 Claims, 6 Drawing Sheets

(51) Int. Cl.
*A61B 1/05* (2006.01)
*A61B 1/07* (2006.01)
*F21V 8/00* (2006.01)
*A61B 1/00* (2006.01)

(56) References Cited

U.S. PATENT DOCUMENTS

| | | | | |
|---|---|---|---|---|
| 2010/0141829 | A1* | 6/2010 | Jalali | G06K 9/2036 |
| | | | | 348/370 |
| 2014/0249369 | A1* | 9/2014 | Hanabusa | A61B 1/00183 |
| | | | | 600/109 |
| 2016/0051126 | A1* | 2/2016 | Troller | A61B 1/0607 |
| | | | | 600/109 |

* cited by examiner

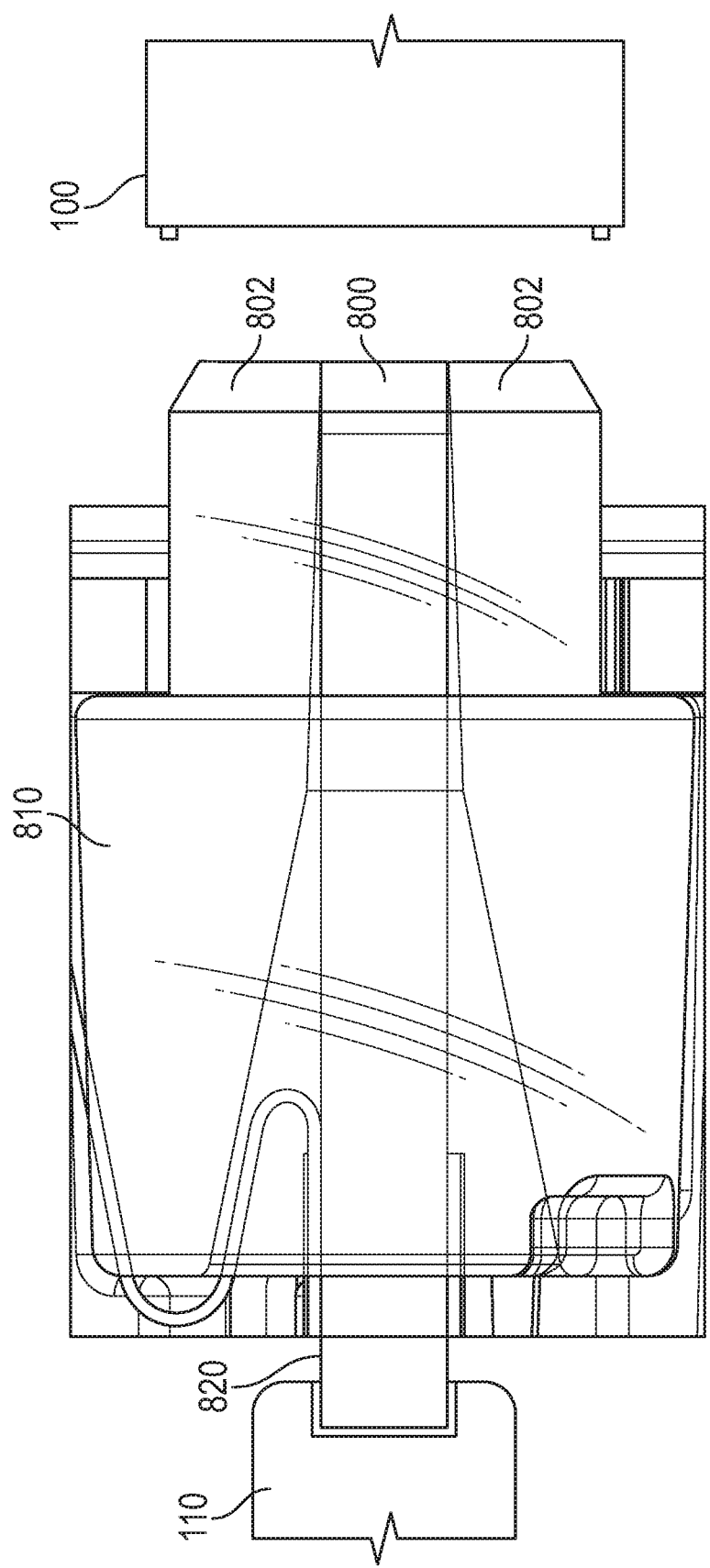

ENDOSCOPE WITH OPTIMIZED ILLUMINATION PATHWAY

This application claims priority from Provisional application No. 62/991,197, filed Dec. 15, 2017; the entire contents of which are herewith incorporated by reference.

BACKGROUND

Clear Image Technology (CIT), the Applicant of this patent application, has developed an arthroscopic system that includes: (a) a disposable scope, (b) a re-usable hand piece, (c) display/console, and (d) software and image enhancement algorithms. CIT's disposable scope is intended to be a single-use digital arthroscope packaged with a sterile drape. The outside diameter of the scope is approximately 2.2 millimeters.

The disposable scope part of this system includes: (a) micro-CMOS camera module (which includes optics) with a ribbon cable style connection, (b) a plastic optical light guide, (c) a stainless steel outer sheath, (d) a printed circuit board embedded in each scope that allows calibration data, (e) electrical contacts to connect with the hand piece, and (g) custom molded plastic parts such as a scope connector and sterile drape cover.

There have been a number of problems and/or drawbacks with the technology prior to the present application. Traditional light sources for endoscopic devices include separate lighting units utilizing halogen or xenon lamps and glass fiber bundles. These are generally bulky and add complexity to the operation. The multiple optical couplings between the light source and working field generate heat and are highly inefficient. As such, these light sources are difficult to miniaturize for a cost-effective, disposable arthroscopic system.

Previous improvements have replaced the traditional lamps with LED arrays, which save some space and improve efficiency. However, the footprint was still relatively large and the continued use of glass fiber bundles necessitated complicated manufacturing processes that were too costly for a disposable device.

SUMMARY

The invention describes a unique system to conduct light efficiently in a compact, cost-effective partly disposable system.

A medical imaging system, is formed of a lighting module, preferably using a single LED. The LED illuminates a reflection chamber, located to receive light from the LED, said reflection chamber terminating in a fiber interfacing surface. An optical fiber connects to the fiber interfacing surface, and receives light therefrom from the interfacing surface the LED is energized. The optical fiber has a first surface connected to the fiber interfacing surface, and has a second surface at an opposite end of the optical fiber from the first surface. A light guide has a first end, optically coupled to the second end of said optical fiber, and the light guide directs light from the first end into a cone shaped surface, that directs light away from a center of the cone shaped surface into a hollow cylindrical shaped surface, creating an illumination by the light at a distal end of the hollow cylindrical shaped surface opposite the first end. A camera, mounted inside the light guide, within an inside of the cylindrical shaped surface images the area illuminated by the light guide.

A method of channeling light to the tip of the endoscope comprises creating light in a first unit, and coupling the light to a fiber interfacing surface; receiving the light into a first end of an optical fiber, connecting the second end of the optical fiber to a light guide, thus coupling the light to a first end of the light guide. In the light guide, the light is directed from the first end around a cone shaped surface in the light guide, to a second end of the light guide, to create a hollow cylindrical shape of light at a second end of the light guide. The hollow cylindrical shape of light at the second end is used to illuminate an endoscopic target. A camera at the second end of the light guide, that is disposed inside the hollow cylindrical shape, is used to receive an image of the illuminated endoscopic target. In an embodiment the optical fiber can be detached from the first unit, and the user can dispose of the optical fiber, and reuse the first unit.

BRIEF DESCRIPTION OF THE DRAWINGS

The different figures show different embodiments.

FIG. 8 shows the proximal end of the illumination guide.

DETAILED DESCRIPTION

Figure 1:
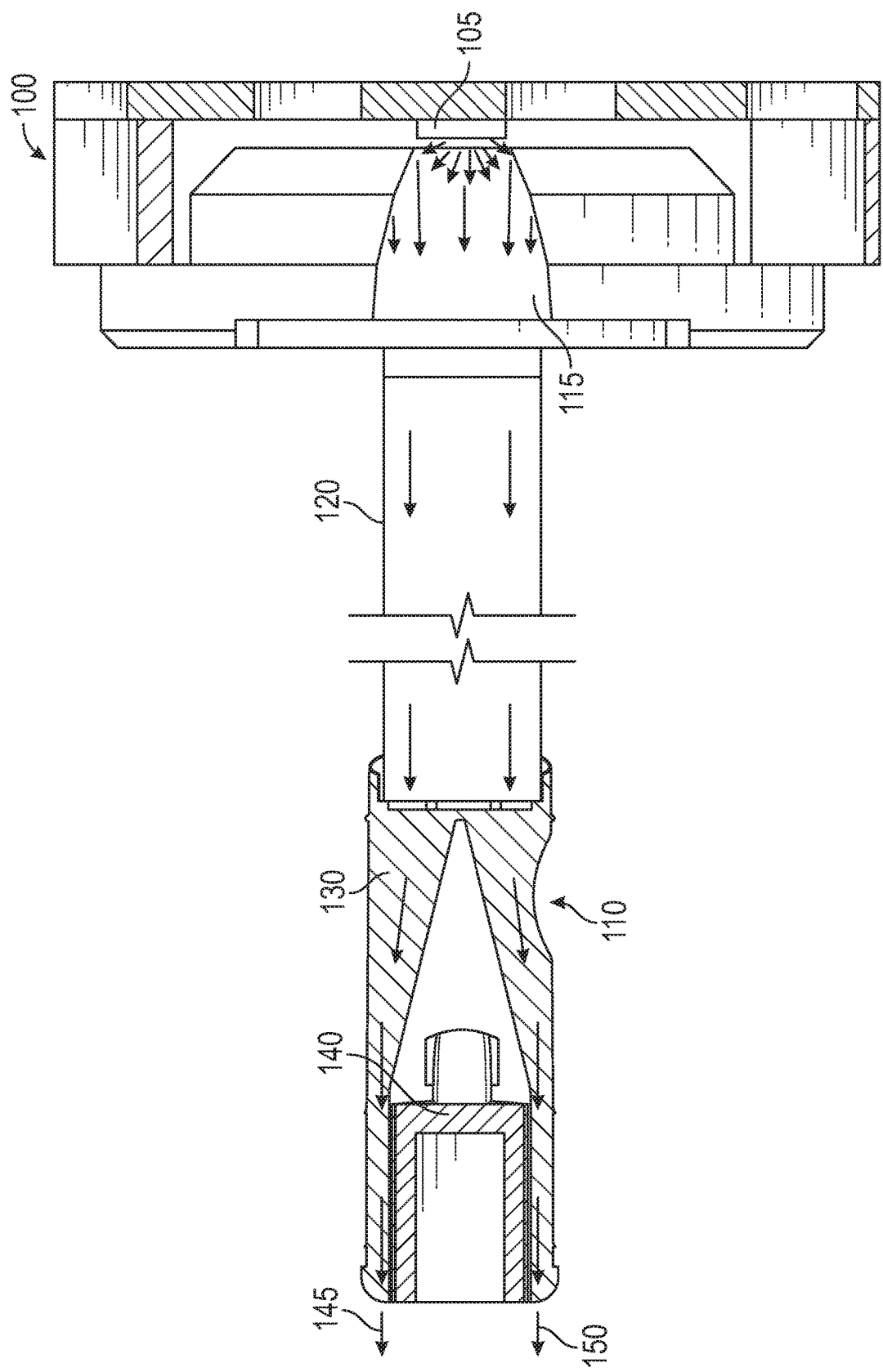
FIG. 1 shows a special endoscope illumination pathway according to embodiments as described herein.

FIG. 1 shows an embodiment showing the complete end to end system, whose details are shown in further detail in the other figures. FIG. 1 shows a single LED-light source 105 within a re-usable hand piece part 100. The Scope Optic Module 110 is contained within a disposable portion of the device.

The LED Module 105 is in the re-usable handpiece 100 which is detachable from the optic module 110. The LED module 105 includes new and specially configured packaging for the LED chip/die as described herein and also includes a reflector cavity 115 filled with an epoxy that is index matched to the plastic optical fiber 120. In an embodiment the epoxy can be Epotek 301, with an n value of 1.519 and the die can be 0.95 mm in size, although larger or smaller size dies can be used. That plastic optical fiber 120 is a single, solid-core plastic optical fiber in the detachable and disposable scope module 110.

The fiber 110 interfaces to a light guide 130 which has a shape to route light from the solid optical fiber 120 around the camera 140 and into a cone-shaped beam 145 coming from the tip 150 of the scope. The light guide in an embodiment can be formed of Eastman Tritan MX711, with an n value of 1.57, or more generally, an n value within 10% of the n value of the fiber 120. The camera 140 at the tip is encapsulated (as described herein) to prevent any stray light entering the back of the sensor from the optical fiber. In an embodiment, the camera is encapsulated with Epotek 353ND black.

The embodiments also describe a solution to auto-orient illumination components for highly efficient coupling between detachable parts.

Figure 2:
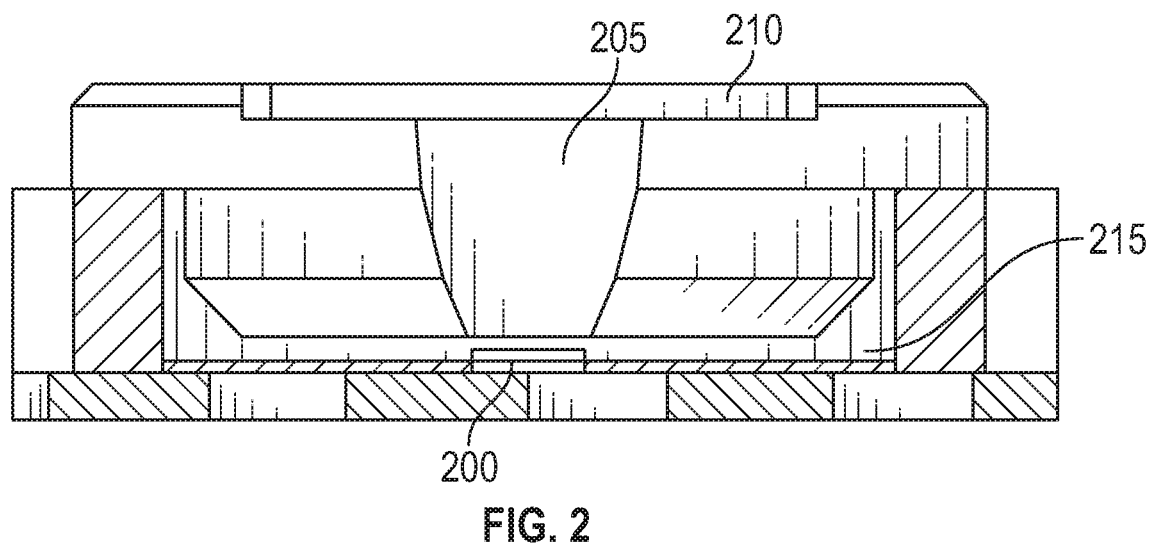
FIG. 2 shows the illumination and LED packaging system.

The LED module 100 is shown in further detail in FIG. 2, and includes a single, white LED light source 200. LED 200 emits light into the reflector cavity 205, which is protected under a flat coverglass 210 of borosilicate material having an n value of 1.517, so again, matched within 10% to the n value of the cavity and the filling epoxy. A printed circuit board PCB 215 houses the electronics used for driving the LED 200.

Use of a single LED is important and novel compared to prior art for a number of reasons. It facilitates significantly reduced power consumption and heat generation compared to a Xenon or halogen source, yet yields similar luminous output and a comparable color spectrum. It also allows integration of the LED in a variety of locations, including the hand piece or scope, since the location can be adjusted as needed. Use of a single LED also minimizes heat generation and simplifies assembly. The illumination pathway can be scaled up or down to accommodate various sizes of sensors.

A special packaging of the LED is used, that is important and novel because it allows fine control over LED parameters such as module glass curvature, index of refraction, and overall package sizing.

In one embodiment, the LED die 200 and reflector cavity 205 are mounted directly to the PCB 215. The module is attached to a metallic connector which can be used to handle the heat distribution. This allows for more efficient heat distribution and integrated optical and electrical connection to the disposable scope. This solution can be customized for other applications and ensure proper color distribution. Further details of the packaging, as described with reference to FIGS. 3A-3B.

A LED module reflector is also located mounted on the PCB 215. This is important and novel compared to the prior art because it redirects light into the fiber 120 to help minimize losses and maximize overall light output. It helps to ensure better coupling efficiency between the LED die 200 and the exterior surface of the module through allowing the encapsulation of the module in index-matched epoxy and optical glass. This also allows more robust mechanical alignment of a detachable light guide fiber to the re-usable source by eliminating intermediary lenses and coupling the fiber directly to the light source.

Figure 3A:
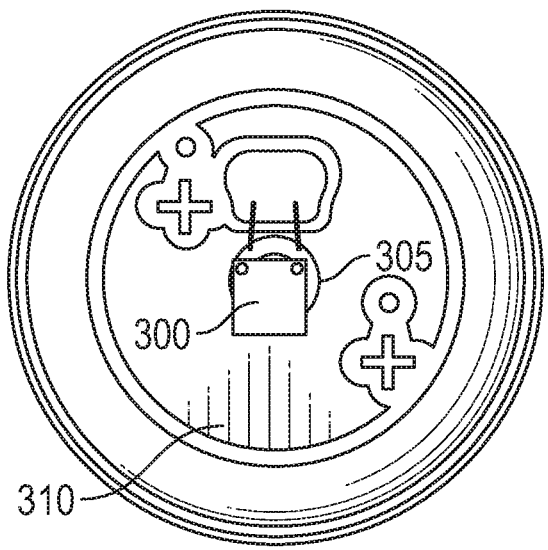
FIGS. 3a and 3B show details of the LED packaging.
Figure 3B:
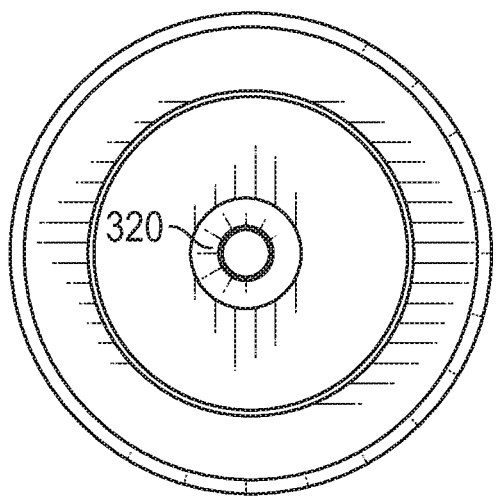

FIG. 3A shows the LED die 300 mounted within a recess 305 on a custom PCB 310, as shown in FIG. 3A. The reflector cavity 320 is mounted over the die in the recess and is filled with epoxy as shown in FIG. 3B. The cavity is sealed with a coverglass 210 that interfaces with the optical fiber of the Scope Optic Module 110.

Figure 4A:
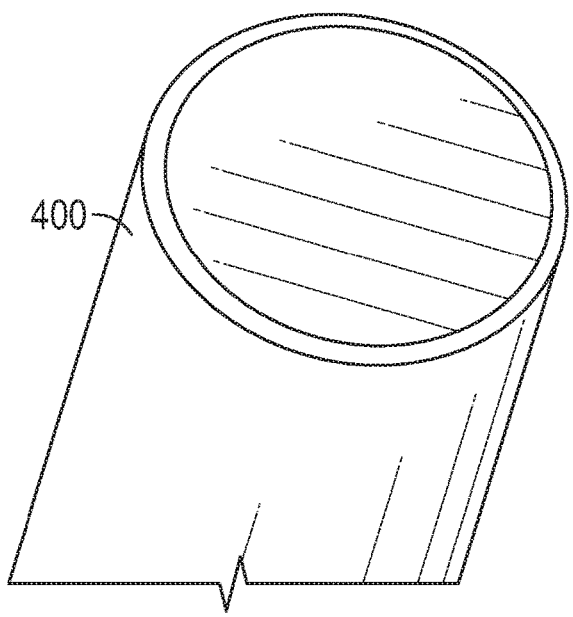
FIGS. 4a and 4B show details of the optical fiber.
Figure 4B:
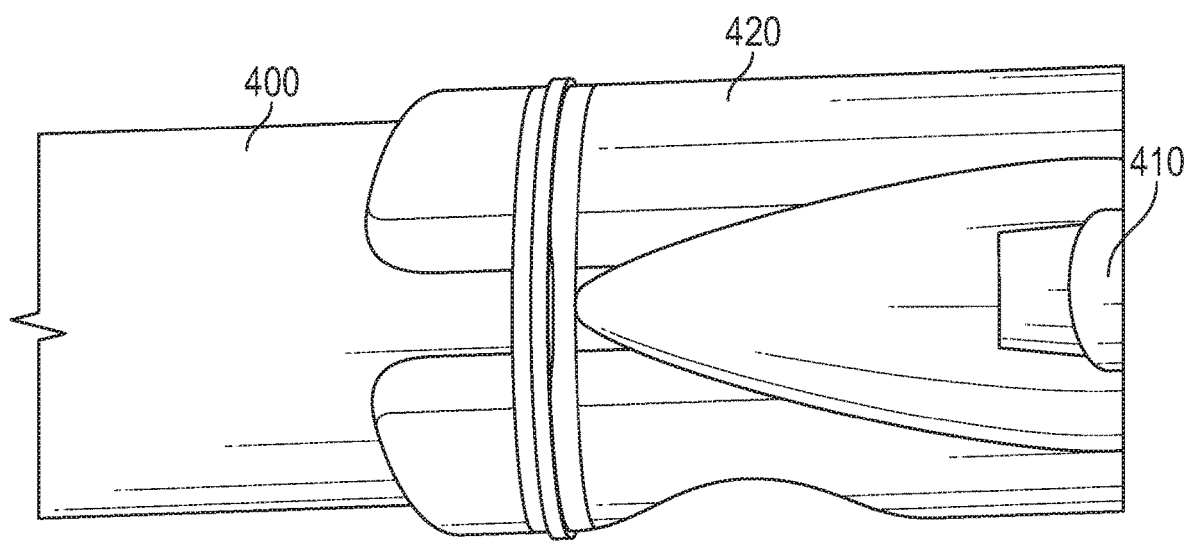

A plastic optical fiber (POF) 400 is used to guide the light to the imaging tip 150 of the scope, as shown in FIGS. 4A-4B. The POF 400 uses a single, solid-core fiber 400 to transmit light from the LED source 100 to the Light Guide 420, which is disposed around the camera at the tip of the scope. Index-matched epoxy is used to fix the optical fiber to the proximal end of the light guide, as shown in FIG. 4B.

This is important and novel because it channels light to the scope tip efficiently. The single fiber is durable and simplifies construction versus multi-filament bundles. Embodiments use fibers that range between 0.25 and 2 mm, preferably 1.74 mm, which are wider than the fiber bundles and small diameter arthroscopic applications used in the prior art. These thicker fibers can ease handling concerns are further reduced as wider diameter fiber is more mechanically robust than thinner fibers. Embodiments can use a Polystyrene-Poly(methyl methacrylate) fiber with a 9/10 core to outer diameter ratio with a numerical aperture of 0.55 and indexes of refraction 1.59/1.49. Another embodiment can use Zeonex/THV (1.53/1.36, aperture of 0.70) and PC/PMMA (1.58/1.49, aperture of 0.53, ratio of 4/5). Again, all the fibers used can be index matched within 10%. The fibers can use ranges of refractive indexes: outer=1.5-1.6, inner=1.3-1.5; the inner and outer portions do not have the same values.

Other embodiments may sue Optical Fibers that may have the values n—1.55-1.59; and dia.—1.8 mm. This is an order of magnitude larger than typical glass fibers which are around 0.05 mm. The preferred material is Polystyrene-Poly (methyl methacrylate)

Embodiments can use cast or extruded fibers. An embodiment uses extruded fibers due to lower cost and easier manufacturing.

The diameter of the plastic fiber matches the diameter of the reflector cavity opening. A single optical fiber is much more efficient coupling to the source as opposed to fiber bundles, allowing use of a single-LED source.

The illumination light guide 420 is fixed to the distal end of the POF 400 and is detachable from the light source.

Figure 5:
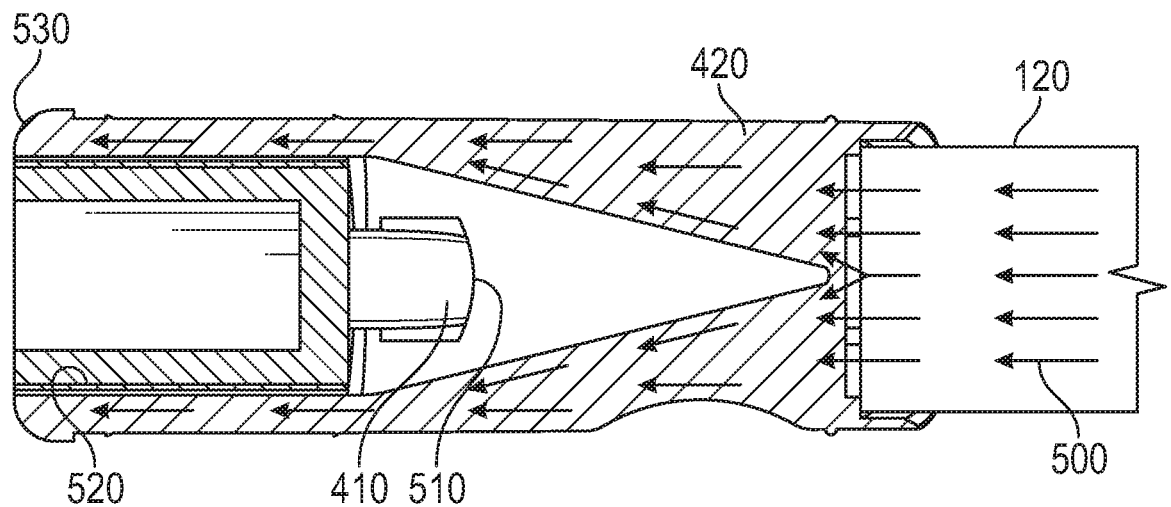
FIG. 5 shows a cutaway view of the optical light guide.

FIG. 5 illustrates the path of travel for light through the Light Guide. Light 500 from the LED source is routed through the fiber 120 into the optical fiber 120, through the light guide 420. The cone-shaped base of the Light Guide 420 directs the light away from the back 510 of the camera sensor 410. The camera 410 is contained within a cavity 520 in the distal portion of the Light Guide 420, allowing light to travel around the camera 410 directly to the target area.

The distal surface 530 of the Light Guide is formed into a lens shape to shape the light and to optimally distribute light to the target of imaging. This can use rounded surfaces on the distal tip with a curvature that creates a convex element. This region is designed to optimally distribute light to illuminate the scene at the focal length of the camera.

The camera uses a cable that is housed within the scope shaft parallel to the fiber. The cable is in contact with the exterior-top surface of the POF, but does not affect transmission of light. That cable is attached to the camera sensor, is routed through the notch in the light guide, through the scope shaft into the scope housing where it is soldered to the PCB.

The thickness range of the fiber is based on the maximum inner diameter of the scope. In an embodiment, the inner diameter dimension of the shaft is 2.1 mm, and the outer dimension of the fiber is 1.74 mm. The extra space allows for the camera cable to run alongside the fiber and prevent damage to either element during installation.

In another embodiment, the camera can communicate its information wirelessly to a receiver, either in the LED module, or in a computer receiving the information. The camera and the LED module or either of them, can be battery operated, e.g., using a "button" style battery.

The light guide is disposable and integrated into the optic module in way that surrounds the camera. Embodiments define the novelty that the single filament construction simplifies assembly compared with bundled glass, allowing a low-cost disposable illumination and visualization component. A single-use light guide ensures every procedure has nominal illumination.

Figure 6:
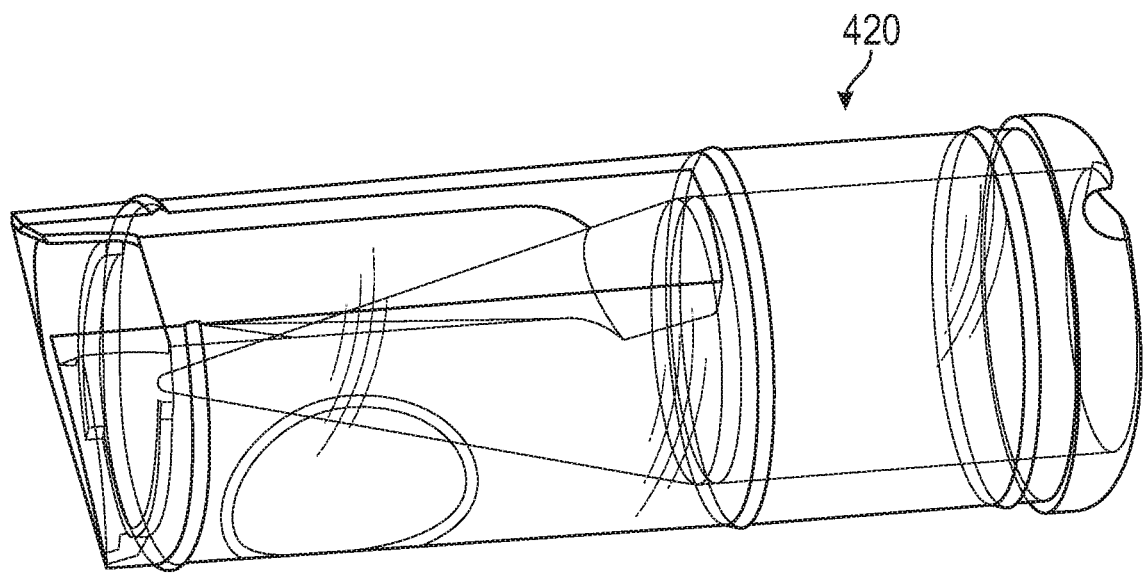
FIG. 6 shows a full view of the light guide.

FIG. 6 shows further details on the light guide 420. The light guide 420 is a single-piece component that is injection molded from transparent, optical grade thermoplastics. The single-piece, thermoplastic light guide round the sensor is also important and novel because the custom molded shape of the distal tip integrates a beam-forming lens function for optimally distributing light on the target. The cone-shaped proximal portion guides light around the camera, blocking it from directly exciting the sensor of the camera. The use of injection molding enables fabrication of the light guide from a mechanically robust material that can withstand orthopedic procedures. The single-body construction of the light guide eliminates the need to assemble and use complex, fragile glass fiber bundles and multiple lenses.

Figure 7A:
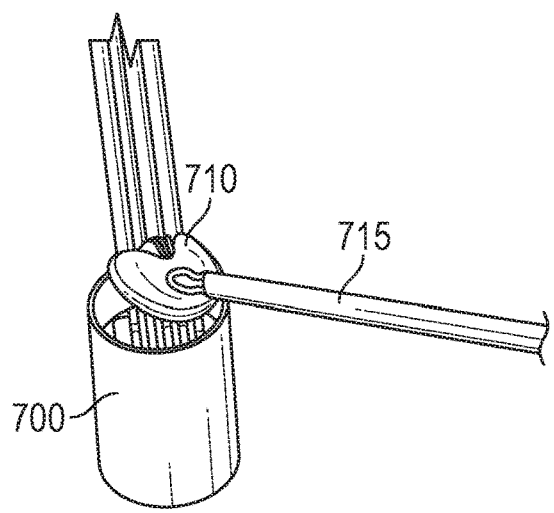
FIGS. 7A, 7B and 7C show details of placing encapsulation material on the camera to black out at least one surface of the camera.
Figure 7B:
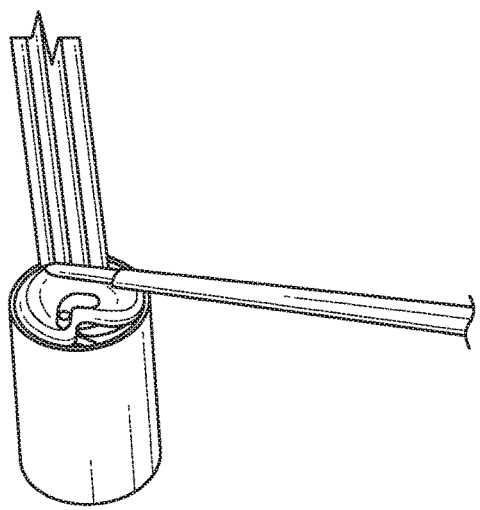
Figure 7C:
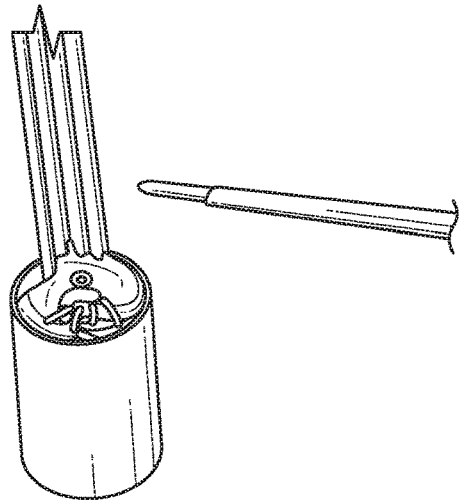

The encapsulation of the camera sensor in the scope is important and novel in its use of optically and spectrally black material to block stray light from entering the camera module. FIG. 7A-7C illustrates the process of how the camera is encapsulated in one embodiment. The camera is inserted into a tube 700, and the opaque encapsulation material is administered as a droplet 710 with a small probe 715, as shown in FIG. 7A. Capillary action allows the droplet of opaque material to fill the entire volume of the tube surrounding the camera, as shown in FIG. 7B. When the opaque filler has cured, the tube is sealed to prevent light entering the camera from the illumination pathway at the proximal surface and to prevent fluid ingress from the distal, patient-facing surface. (FIG. 7). The illumination optical fiber is positioned directly behind the camera and stray light from behind can affect the sensor directly without encapsulation, interfering with the image.

The encapsulation process simplifies assembly of the module at the tip by simultaneously sealing the camera in the tube for a more reproducible process. Additionally, encapsulation protects the camera module from damage during subsequent assembly processes. Our procedure for encapsulation with the camera recessed into the tube 400 fixes the camera within the mounting tube in a manner that prevents the opaque adhesive from contacting other optical elements.

FIG. 8 shows the fiber support at the proximal end of the illumination optical fiber that couples directly to the LED module 100 and ensures optimal alignment of the fiber in each detachable scope. The custom fiber support for the plastic optical fiber is important and novel because it allows better alignment of the optical fiber and the LED module during assembly and desired use. It also protects the edges of the fiber from side impacts and other damage during insertion of the scope to the handpiece. Our novel illumination pathway minimizes light loss between the source and the tip of the scope.

The light guide also results in optimal light distribution. Together, these factors mean that a high quality image can be achieved with fewer, simpler, and less expensive optical components. There is also a reduction in localized heat affecting either the patient or the operator. The illumination pathway can be scaled for various sizes of image sensors.

In FIG. 8, 800 is the optical fiber. 802 is the fiber support, which is a molded plastic piece that holds the fiber in place and aligns the fiber to the LED when the scope is assembled to the light source. The fiber support 802 fits to corresponding surfaces on the cover glass 210. There is also a molded plastic component around the LED reflector that receives the fiber support. The fiber support 810 fits over the fiber support 802 to hold the fiber in position and the fiber end 820 exits the second fiber support where it is coupled to the part 110, and spaced therefrom, e.g., by 100 mm. In one embodiment, the fiber supports 802, 810 can be a single piece.

Although only a few embodiments have been disclosed in detail above, other embodiments are possible and the inventors intend these to be encompassed within this specification. The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A medical imaging system, comprising:
   a lighting module, formed of a circuit board having a recess in the circuit board, an LED chip, mounted in the recess on the circuit board, an LED module reflector, formed of a hollow reflector filled with index matched filler material, the LED module reflector mounted on and above the circuit board, with all surfaces of the LED module reflector being over the LED chip and positioned so that light from the LED chip passes in a direction away from the circuit board, toward and through the LED module reflector, and electronics used for driving the LED chip to emit said light, said electronics also being housed on the circuit board;
   an optical fiber, receiving light from the LED chip when said LED chip is energized,
   where the LED module reflector directs light into the fiber through the LED module reflector;
   said optical fiber having a first surface lacing to the LED module reflector, and having a second surface at an opposite end of the optical fiber from the first surface;
   a light guide, having a first end, optically coupled to said second end of said optical fiber, and said light guide directing light to a second end, and a camera, mounted inside the light guide, within the hollow interior surface of the cylindrical shaped surface, said camera having an imaging end facing toward said second end of the light guide, and receiving an image that is illuminated by the light guide, wherein the reflection chamber is filled with a solid material that index matches to said optical fiber within 10%.

2. The system as in claim 1, wherein the camera has a rear end opposite to the imaging end, and further comprising an encapsulation material covering the rear end of the camera, preventing light coming from said rear end through said light guide from reaching the camera.

3. The system as in claim 2, wherein said encapsulation material is a black material.

4. The system as in claim 2, further comprising a tube into which the camera is inserted, and a rear end of the tube is filled with said encapsulation material.

5. The system as in claim 1, wherein the LED chip is attached to a metallic connector which handles heat distribution.

6. The system as in claim 1, wherein the light guide has a first inner section that is conical and directs light in the light guide away from the conical inner section, and a second section, that is cylindrical and forms a cylindrical inner section, and is connected to the first section, and where the camera has a cylindrical outer housing, sized to fit in the cylindrical second section, and held within the cylindrical inner section.

7. The system as in claim 1, wherein the circuit board includes a printed circuit board.

8. A medical imaging system, comprising:
   a lighting module, formed of a circuit board having a recess in the circuit board, an LED chip, mounted in the recess on the circuit board, an LED module reflector, formed of a hollow reflector filled with index matched filler material, the LED module reflector mounted on and above the circuit board, with all surfaces of the LED module reflector being over the LED chip and positioned so that light from the LED chip passes in a direction away from the circuit board, toward and through the LED module reflector, and electronics used for driving the LED chip to emit said light, said electronics also being housed on the circuit board;

an optical liber, receiving light from the LED chip when said LED chip is energized, where the LED module reflector directs light into the fiber through the LED module reflector;

said optical fiber having a first surface facing to the LLP module reflector, and having a second surface at an opposite end of the optical fiber from the first surface;

a light guide, having a first end, optically coupled to said second end of said optical fiber, and said light guide directing light to a second end, and a camera, mounted inside the light guide, within the hollow interior surface of the cylindrical shaped surface, said camera having an imaging end facing toward said second end of the light guide, and receiving an image that is illuminated by the light guide, wherein the light guide is a single piece component that is injection molding from transparent thermoplastic material that index matches within 10% to an optical index of the fiber.

9. The system as in claim 8, wherein the index matched filler material in the LED module reflector is index matched epoxy.

10. The system as in claim 8, wherein the distal end of the light guide is rounded to carry out a lensing operation.

11. The system as in claim 8, wherein the optical fiber is a single optical fiber.

12. An optical imaging system, comprising:
a light source assembly formed of a circuit board, having a recess in the circuit board, an LED chip, mounted in the recess on the circuit board, and an LED module reflector, formed of a hollow reflector filled with index matched filler material, the LED module reflector mounted on and over the circuit board, with all surfaces of the LED module reflector being over the LED chip, and electronics used for driving the LED chip to emit said light, said electronics also being housed on the circuit board;

an optical liber, receiving light from the LED chip when said LED chip is energized, where the LED module reflector redirects light from the LED chip into the optical fiber;

a light guide, having a first end optically coupled to said optical fiber, and said light guide having a cylindrical shape at said first end, a camera, mounted inside the hollow cylindrical shape at the second end of the light guide, said camera having an imaging end facing toward said second end of the light guide, wherein the light guide is a single piece component that is injection molding from transparent thermoplastic material.

13. The system as in claim 12, wherein the index matched filler material in the LED module reflector is index matched epoxy.

14. The system as in claim 12, wherein the camera has a rear end opposite to the imaging end, and further comprising an encapsulation material covering the rear end of the camera, preventing light coming from said rear end through said cone shaped surface from reaching the camera.

15. The system as in claim 12, wherein the light guide has a first inner section that is conical and directs light in the light guide away from the conical inner section, and a second section, that is cylindrical and forms a cylindrical inner section, and is connected to the first section, and where the camera has a cylindrical outer housing, sized to fit in the cylindrical second section, and held within the cylindrical inner section.

16. The system as in claim 12, wherein a distal end of the light guide is rounded to carry out a lensing operation.

* * * * *